(12) United States Patent
Abbitt

(10) Patent No.: US 9,587,243 B2
(45) Date of Patent: *Mar. 7, 2017

(54) UBIQUITIN REGULATORY ELEMENTS

(71) Applicant: PIONEER HI BRED INTERNATIONAL INC, Johnston, IA (US)

(72) Inventor: Shane Abbitt, Ankeny, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 30 days.

This patent is subject to a terminal disclaimer.

(21) Appl. No.: 14/539,673

(22) Filed: Nov. 12, 2014

(65) Prior Publication Data

US 2015/0128302 A1    May 7, 2015

Related U.S. Application Data

(60) Continuation of application No. 13/775,341, filed on Feb. 25, 2013, now abandoned, which is a continuation of application No. 13/429,576, filed on Mar. 26, 2012, now Pat. No. 8,420,797, which is a division of application No. 12/539,137, filed on Aug. 11, 2009, now Pat. No. 8,168,859.

(60) Provisional application No. 61/092,205, filed on Aug. 27, 2008.

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 15/823* (2013.01); *C12N 15/8223* (2013.01)

(58) Field of Classification Search
None
See application file for complete search history.

(56) References Cited

U.S. PATENT DOCUMENTS 8,168,859 B2 *  5/2012  Abbitt ................ C12N 15/8223
                                                435/320.1
8,420,797 B2 *  4/2013  Abbitt ................ C12N 15/8223
                                                435/320.1

* cited by examiner

*Primary Examiner* — Brent Page
(74) *Attorney, Agent, or Firm* — Pioneer Hi-Bred Intl. Inc.

(57) ABSTRACT

The present invention provides compositions and methods for regulating expression of heterologous nucleotide sequences in a plant. Compositions are novel nucleotide sequences for a constitutive regulatory element isolated from *sorghum*. A method for expressing a heterologous nucleotide sequence in a plant using the regulatory sequences disclosed herein is provided. The method comprises transforming a plant cell to comprise a heterologous nucleotide sequence operably linked to one or more of the regulatory sequences of the present invention and regenerating a stably transformed plant from the transformed plant cell.

11 Claims, 4 Drawing Sheets

CTGCCCTTAAGGCCAATTGTTCAAGATTCATTCAACAATTGAAACATCTCCCA
TGATTAAATCAGTATAAGGTTGCTATGGTCTTGCTTGACAAAGTTTTTTTTG
AGGGAATTTCAACTAAATTTTTGAGTGAAACTATCAAATACTGATTTTAAAAA
ATTTTTATAAAAGGAAGCGCAGAGATAAAAGGCCATCTATGCTACAAAAGTA
CCCAAAAATGTAATCCTAAAGTATGAATTGCATTTTTTTTTGTTTGGACGAA
AGGAAAGGAGTATTACCACAAGAATGATATCATCTTCATATTTAGATCTTTT
TGGGTAAAGCTTGAGATTCTCTAAATATAGAGAAATCAGAAGAAAAAAAAA
CCGTGTTTTGGTGGTTTTGATTTCTAGCCTCCACAATAACTTTGACGGCGTCG
ACAAGTCTAACGGACACCAAGCAGCGAACCACCAGCGCCGAGCCAAGCGAA
GCAGACGGCCGAGACGTTGACACCTTCGGCGCGGCATCTCTCGAGAGTTCCG
CTCCGGCGCTCCACCTCCACCGCTGGCGGTTTCTTATTCCGTTCCGTTCCGCCT
CCTGCTCTGCTCCTCTCCACACCACACGGCACGAAACCGTTACGGCACCGGC
AGCACCCAGCACGGGAGAGGGGATTCCTTTCCCACCGTTCCTTCCCTTTCCGC
CCCGCCGCTATAAATAGCCAGCCCCATCCCCAGCTTTTTTCCCCAATCTCATC
TCCTCTCTCCTGTTGTTCGGAGCACACGCACAATCCGATCGATCCCCAAATCC
CCTTCGTCTCTCCTCGCGAGCCTCGTGGATCCCAGCTTCAAG<u>GTACGGCGATC
GATCATCCCCCCTCCTTCTCTCTACCTTCTTTTCTCTAGACTACATCGGATGGC
GATCCATGGTTAGGGCCTGCTAGTTTCCCTTCCTGTTTTGTCGATGGCTGCGA
GGCACAATAGATCTGATGGCGTTATGACGGCTAACTTGTCATGTTGTTGCGAT
TTATAGTCCCTTTAGGAGATCAGTTTAATTTCTCGGATGGTTCGAGATCGGTG
GTCCATGGTTAGTACCCTAAGATCCGCGCTGTTAGGGTTCGTAGATGGAGGC
GACCTGTTCTGATTGTTAACTTGTCAGTACCTGGGAAATCCTGGGATGGTTCT
AGCTCGTCCGCAGATGAGATCGATTTCATGATCCTCTGTATCTTGTTTCGTTG
CCTAGGTTCCGTCTAATCTATCCGTGGTATGATGTAGATGTTTGATCGTGCT
AACTACGTCTTGTAAAGTTAATTGTCAGGTCATAATTTTTAGCATGCCTTTTTT
TTTGTTTGGTTTTGTCTAATTGGGCTGTCGTTCTAGATCAGAGTAGAAGACTG
TTCCAAACTACCTGCTGGATTTATTGAACTTGGATCTGTATGTGTGTCACATA
TCTTCATAAATTCATGATTAAGATGGATTGAAATATCTTTTATCTTTTTGGTAT
GGATAGTTCTATATGTTGGTGTGGCTTTGTTAGATGTATACATGCTTAGATAC
ATGAAGCAACGTGCTGCTACTGTTTAGTAATTGCTGTTCATTTGTCTAATAAA
CAGATAAGGATATGTATTTATGTTGCTGTTGGTTTTGCTGGTACTTTGTTGGAT
ACAAATGCTTCAATACAGAAACAGCATGCTGCTACGATTTACCATTTATCTA
ATCTTATCATATGTCTAATCTAATAAACAAACATGCTTTTAAATTATCTTCAT
ATGCTTGGATGATGGCATACACAGCGGCTATGTGTGGTTTTTAAATACCCAG
CATCATGGGCATGCATGACACTGCTTTAATATGCTTTTATTTGCTTGAGACT
GTTTCTTTTGTTTATACTGACCCTTTAGTTCGGTGACTCTTCTGCAG</u>

Fig. 1

```
                    1                                               50
SEQ ID NO: 4   (1)  TGCAGTGCAGCGTGACCCGGTCGTGCCCCTCTCTAGAGATAATGAGCATT
SEQ ID NO: 1   (1)  --------------------------------------------------
   Consensus   (1)
                    51                                              100
SEQ ID NO: 4  (51)  GCATGTCTAAGTTATAAAAAATTACCACATATTTTTTTTGTCACACTTGT
SEQ ID NO: 1   (1)  --------------------------------------------------
   Consensus  (51)
                    101                                             150
SEQ ID NO: 4 (101)  TTGAAGTGCAGTTTATCTATCTTTATACATATATTTAAACTTTACTCTAC
SEQ ID NO: 1   (1)  -------------------------------------CTGCCCT-TAA
   Consensus (101)                                       CT   CT  TA
                    151                                             200
SEQ ID NO: 4 (151)  GAATAATATAATCTATAGTACTACAATAATATCAGTGTTTAGAGAATCA
SEQ ID NO: 1  (11)  GGCCAAT-TGTTCAAGATTCATTCAACAATTGAAACATCTCCCATGATTA
   Consensus (151)  G   AAT T  TC A T  T CAA AAT  A  T T  A  AT A
                    201                                             250
SEQ ID NO: 4 (201)  TATAAATGAACAGTTAGACATGGTCTAAAG-GACAATTGAGTATTTTGAC
SEQ ID NO: 1  (60)  AATCAGT-ATAAGGTTGCTATGGTCTTGCTTGACAAGTTTTTTTTTGAG
   Consensus (201)  AT A A  AG T G ATGGTCT      GACAA   T TTTTGA
                    251                                             300
SEQ ID NO: 4 (250)  AACAGGACTCTACAGTTTTATCTTTTTAGTGTGCATGTGTTCTCCTTTTT
SEQ ID NO: 1 (109)  ----GGAATTT-CAACTAAAT-TTTGAGTGAAACTATCAAATACTGATT
   Consensus (251)      GGA T T  CA T  AT TTTT AGTG      T T   T CT TT
                    301                                             350
SEQ ID NO: 4 (300)  TTTTGCAAATAGCTTCACCTATATAATACTTCATCCATTTTATTAGTACA
SEQ ID NO: 1 (153)  TT----AAAAATTTT---TATAAAGGAAGCGCAGAGATAAAGG----
   Consensus (301)  TT    AAA A TT    TATA AA    C    A TA G
                    351                                             400
SEQ ID NO: 4 (350)  TCCATTAGGGTTTAGGGTTAATGGTTTTTATAGACTAATTTTTTAGTA
SEQ ID NO: 1 (192)  -CCATCTATGCTACA------AAAGTACCCAAAATGTAATCCTAAAGT-
   Consensus (351)   CCAT TA G T  A         A GT   A  A  T   AGT
                    401                                             450
SEQ ID NO: 4 (400)  CATCTATTTTATTCTATTTTTAGCCTCTAAATTAAGAAAACTAAAACTCTA
SEQ ID NO: 1 (234)  -ATGAATTGCATTTTTTTTTGTTTGGACGAAAGGAAAGGAGTATTACCA
   Consensus (401)   AT  ATT ATT T TTTT G T  A    A GAAA    A   C A
                    451                                             500
SEQ ID NO: 4 (450)  TTTTAGTTTTTTTATTTAATAATTTAGATATAAAATAGAATAAAATAAAG
SEQ ID NO: 1 (283)  CAAGAATGATATCATCTTCATATTTAGATCTTTTTTGGGTAAAGCTTGAG
   Consensus (451)   A  T  T ATT T    ATTTAGAT T    T G AA T   AG
                    501                                             550
SEQ ID NO: 4 (500)  TGACTAAAAAT-TAAACAAATACCCTTTAAGAAATTAAAAAAACTAAGGA
SEQ ID NO: 1 (333)  ATTCTCTAAATATAGAGAAATC-------AGAAGAAAAAAAAAACCGTG--
   Consensus (501)      CT AAAT TA A AAAT         AGAA    AAAAAAAC   G
                    551                                             600
SEQ ID NO: 4 (549)  AACATTTTTCTTGTTTCGAGTAGATAATGCCAGCCTG--TTAAACGCCGT
SEQ ID NO: 1 (374)  ----TTTTGGTGGTTTGATTTCTAGCCTCCACAATAACTTTGACGGCGT
   Consensus (551)      TTTT T GTTT GA T          CCA  T  TT ACG CGT
                    601                                             650
SEQ ID NO: 4 (597)  CGACGAGTCTAACGGACACCAACCAGCGAACCAGCAGCGTCGCGTCGGGC
SEQ ID NO: 1 (420)  CGACAAGTCTAACGGACACCAAGCAGCGAACCACCAGCGCCGAG-----C
   Consensus (601)  CGAC AGTCTAACGGACACCAA CAGCGAACCA CAGCG CG G      C
                    651                                             700
SEQ ID NO: 4 (647)  CAAGCGAAGCAGACGGCACGGCATCTCTGTCGCTGCCTCTGGACCCCTCT
SEQ ID NO: 1 (465)  CAAGCGAAGCAGACGGC-CGAGACGTTGACACCTTCGGCGCGGCATCTCT
   Consensus (651)  CAAGCGAAGCAGACGGC CG  A T    CT C  C G C  CTCT
                    701                                             750
SEQ ID NO: 4 (697)  CGAGAGTTCCGCTCCACCGTTGGACTTGCTCCGCTGTCGGCATCCAGAAA
SEQ ID NO: 1 (514)  CGAGAGTTCCGCTCCGGCGCTCCACCTCCACCGCTGGCGGTTTC---TTA
   Consensus (701)  CGAGAGTTCCGCTCC  CG T  AC T C  CCGCTG CGG  TC    A
                    751                                             800
SEQ ID NO: 4 (747)  TTGCGTGGCGGAGCGGCAGACGTGAGCCGGCACGGCAGGCGGC-CTCCTC
SEQ ID NO: 1 (561)  TTCCGTTCCGTTCCGCCTCCTGCTCTGCTCCTCTCCACACCACACGGCAC
   Consensus (751)  TT CGT  CG  CG C  G         C   CC CA C  CC CC
```

Fig. 2A

```
                       801                                             850
SEQ ID NO: 4   (796)   CTCCTC-TCACGGCACCGGCAGCT------ACGGG-----GGATTCCTTT
SEQ ID NO: 1   (611)   GAAACCGTTACGGCACCGGCAGCACCCAGCACGGGAGAGGGGATTCCTTT
  Consensus    (801)         C T ACGGCACCGGCAGC      ACGGG     GGATTCCTTT
                       851                                             900
SEQ ID NO: 4   (834)   CCCACCGCTCCTTCGCTTTCCCTTCCTCGCCCGCCGTAATAAATAGACAC
SEQ ID NO: 1   (661)   CCCACCGTTCCTTCCCTTTCCGC------CCCGCCGCTATAAATAGCCAG
  Consensus    (851)   CCCACCG TCCTTC CTTTCC       CCCGCCG ATAAATAG CA
                       901                                             950
SEQ ID NO: 4   (884)   CCCC-TCCACACCCTCTTTCCCCAACCTCGT-----------GTTGTTC
SEQ ID NO: 1   (705)   CCCCATCCCCAGCTTTTTTCCCAATCTCATCCCTCTCTCCTGTTGTTC
  Consensus    (901)   CCCC TCC CA C T TTTCCCCAA CTC T             GTTGTTC
                       951                                            1000
SEQ ID NO: 4   (921)   GGAGCGCACACACACACAA--------CCAGATCTCCCCCAAATCCACCC
SEQ ID NO: 1   (755)   GGAGCACACGCACAATCCGATCGATCCCCAAATCCCTTCGTCTCTCCTC
  Consensus    (951)   GGAGC CAC CACA  C           CCA ATC CC  C  TC  C C
                       1001                                           1050
SEQ ID NO: 4   (963)   G------TCG-GCACCTCCGCTTCAAGGTACGCCGCTCG-TCCTCCCCCC
SEQ ID NO: 1   (805)   GCGAGCCTCGTGGATCCCAGCTTCAAGGTACGCGATCGATCATCCCCCC
  Consensus    (1001)  G      TCG G  C C  GCTTCAAGGTACG CG TCG TC TCCCCCC
                       1051                                           1100
SEQ ID NO: 4   (1005)  CCCCCCCTCTCTACCTTCT-----CTAGATCGGCGTTCCGGTCCATGCATG
SEQ ID NO: 1   (855)   TCCTTCTCTCTACCTTCTTTTCTCTAGACTACATCGGATGGCGATCCATG
  Consensus    (1051)  CC CTCTCTACCTTCT     CTAGA          G C AT CATG
                       1101                                           1150
SEQ ID NO: 4   (1050)  GTTAGGGCCCGGTAGTTCTACTTC-TGTT--------------------
SEQ ID NO: 1   (905)   GTTAGGGCCTGCTAGTTTCCCTTCCTGTTTGTCGATGGCTGCGAGGCAC
  Consensus    (1101)  GTTAGGGCC G TAGTT   CTTC TGTT
                       1151                                           1200
SEQ ID NO: 4   (1078)  ------------------------------CATGTTTGTG----TT
SEQ ID NO: 1   (955)   AATAGATCTGATGGCGTTATGACGGCTAACTTGTCATGTTGTTGCGATTT
  Consensus    (1151)                                CATGTT TG    TT
                       1201                                           1250
SEQ ID NO: 4   (1090)  A-------------GATCCGTGT-----------TTGTGTTAGATCCGT
SEQ ID NO: 1   (1005)  ATAGTCCCTTTAGGAGATCAGTTTAATTTCTCGGATGGTTCGAGATCCGT
  Consensus    (1201)  A             GATC GT T          T GT  AGATC GT
                       1251                                           1300
SEQ ID NO: 4   (1115)  GCTGCTAGCGTTCGTACACG--GATGCGACCTGTACG---TCA-------
SEQ ID NO: 1   (1055)  GGTCC-ATGGTTAGTACCCTAAGATCCGCGCTGTTAGGGTTCGTAGATGG
  Consensus    (1251)  G T C A  GTT GTAC C   GAT CG CTGT G   TC
                       1301                                           1350
SEQ ID NO: 4   (1153)  ----GACACGTTCTGATTGCTAACTTGCCAGTGTTTCTCTTTGGGGAATC
SEQ ID NO: 1   (1104)  AGGCGACCTGTTCTGATTGTTAACTTGTCAGTACCT------GGGAAATC
  Consensus    (1301)       GAC GTTCTGATTG TAACTTG CAGT  T       GGG AATC
                       1351                                           1400
SEQ ID NO: 4   (1199)  CTGGGATGGCTCTAGCCGTTCCGCAGACGGGATCGATTTCATGATTTTTT
SEQ ID NO: 1   (1148)  CTGGGATGGTTCTAGCTCGTCCGCAGATGAGATCGATTTCATGATCCTCT
  Consensus    (1351)  CTGGGATGG TCTAGC  TCCGCAGA G GATCGATTTCATGAT  T T
                       1401                                           1450
SEQ ID NO: 4   (1249)  -----TTGTTTCGTTGCATAGGGTTTGGTTTGCCCTTTTCCT----TTAT
SEQ ID NO: 1   (1198)  GTATCTTGTTTCGTTGCCTAGG-TTCCGTCTAATCTATCCGTGGTATGAT
  Consensus    (1401)       TTGTTTCGTTGC TAGG TT GT T CT T CT    T AT
                       1451                                           1500
SEQ ID NO: 4   (1290)  TTCAATATATGC--CGTGCA--------CTTGT--------TTGTCGGGT
SEQ ID NO: 1   (1247)  GTAGATGTTTGATCGTGCTAACTACGTCTTGTAAAGTTAATTGTCAGGT
  Consensus    (1451)  T AT T T    CGTGC        CTTGT         TTGTC GGT
                       1501                                           1550
SEQ ID NO: 4   (1322)  CATCTTTTCATGCTTTTTTTTGTCTTGGTTGTGATGATGTGGTCTGGTTG
SEQ ID NO: 1   (1297)  CATAATTTTTAGCATGCCTTTTTTTTGTT----TGGTTTGTCTAATTG
  Consensus    (1501)  CAT  TTT GC T   TTT T TT GTT       TG T T GTCT  TTG
                       1551                                           1600
SEQ ID NO: 4   (1372)  GGCGGTCGTTCTAGATCGGAGTAGAATTCTGTTTCAAACTACCTGGTGGA
SEQ ID NO: 1   (1343)  GGCTGTCGTTCTAGATCAGAGTAGAAGACTGTTCCAAACTACCTGCTGGA
  Consensus    (1551)  GGC GTCGTTCTAGATC GAGTAGAA  CTGTT CAAACTACCTG TGGA
```

Fig. 2B

```
                       1601                                          1650
SEQ ID NO: 4  (1422)   TTTATTAATTTTGGATCTGTATGTGTGTGCCATACATATTCATAGTTACG
SEQ ID NO: 1  (1393)   TTTATTGAACTTGGATCTGTATGTGTGT--CACATATCTTCATAAATTCA
   Consensus  (1601)   TTTATT A  TTGGATCTGTATGTGTGT  CA A AT TTCATA  T C
                       1651                                          1700
SEQ ID NO: 4  (1472)   AATTGAAGATGATGGATGGAAATATCGATCTAGGATAGGTATACATGTTG
SEQ ID NO: 1  (1441)   --T-GATTAAGATGGATTGAAATATCTTT---------TAT-CTTTTTG
   Consensus  (1651)      T GA A GATGGAT GAAATATC  T           TAT C T TTG
                       1701                                          1750
SEQ ID NO: 4  (1522)   ATGCGGGTTTTACTGATGCATATACAGAGATGCTTTTTGTTCGCTTGGTT
SEQ ID NO: 1  (1477)   GT------------ATGGATA-------GTTCTATATGTTGGTGTGGCT
   Consensus  (1701)    T            ATG ATA       T CT T TGTT G  TGG T
                       1751                                          1800
SEQ ID NO: 4  (1572)   GTGAT-GATGTGGTGTGGTTGGGCGGTCGTTCATTCGTTCTAGATCGGAG
SEQ ID NO: 1  (1507)   TTGTTAGATGTA----------------TACATGCTT---AGATACATG
   Consensus  (1751)    TG T GATGT                  T CAT C T   AGAT    G
                       1801                                          1850
SEQ ID NO: 4  (1621)   TAGAATACTGTTTCAAACTACCTGGTGTATTTATTAATTTTTGGAACTGTA
SEQ ID NO: 1  (1537)   AAGCAACGTGCTGCTA-----CTG-----TTTAGTAATTG-----CTGTT
   Consensus  (1801)    AG A   TG T C A     CTG      TTTA TAATT      CTGT
                       1851                                          1900
SEQ ID NO: 4  (1671)   TGTGTGTGTCATACATCTTCATAGTTACGAGTTTAAGATGGATGGAAATA
SEQ ID NO: 1  (1572)   CATTTGTCTAATA------------AACAGATAAGGAT--ATGTATTTA
   Consensus  (1851)      T TGT T ATA            A  AG T  GAT  ATG A  TA
                       1901                                          1950
SEQ ID NO: 4  (1721)   TCGATCTAGGATAGGTATACATGTTGATGTGGGTTTTACTGATGCAT--A
SEQ ID NO: 1  (1607)   TGTTGCTG---TTGGTTTTGCTGGTACTTTGTTGGATACAAATGCTTCAA
   Consensus  (1901)   T   CT    T GGT T   TG T T TG   TAC ATGC T   A
                       1951                                          2000
SEQ ID NO: 4  (1769)   TACATGATGGCATATGCAGCATCTATTCATA--TGCTCTAACCTTGAGTA
SEQ ID NO: 1  (1654)   TACAGAAAACAGCATGCTGCTACGATTTACCATTTATCTAACTT-ATCA
   Consensus  (1951)   TACA A    ATGC GC  C ATT A   T   TCTAA CTT A  A
                       2001                                          2050
SEQ ID NO: 4  (1817)   CCTATCTATTATAATAAACAAGTATGTTTTATAATTATTTTGATCTTGAT
SEQ ID NO: 1  (1703)   TATGTCTAATCTAATAAACAAACATGCTTTAAATTAT------CTTCAT
   Consensus  (2001)    T TCTA T TAATAAACAA  ATG TTT  AATTAT       CTT AT
                       2051                                          2100
SEQ ID NO: 4  (1867)   ATACTTGGATGATGGCATATGCAGCAGCTATATGTGGATTTTTT--TAGC
SEQ ID NO: 1  (1747)   ATGCTTGGATGATGGCATACACAGCGGCTATGTGTGGTTTTTTAAATACC
   Consensus  (2051)   AT CTTGGATGATGGCATA  CAGC GCTAT TGTGG TTTTT   TA C
                       2101                                          2150
SEQ ID NO: 4  (1915)   C---------------------CTGCCTTCATACGCTATTTATTTGCTT
SEQ ID NO: 1  (1797)   CAGCATCATGGGCATGCATGACACTGCTTTAATATGCTTTTTATTTGCTT
   Consensus  (2101)   C                     CTGC TT ATA GCT TTTATTTGCTT
                       2151                                          2200
SEQ ID NO: 4  (1943)   GGTACTGTTTCTTTTGTCGATGCTCACCCTGTTGTTGGTGTTACTTCTG
SEQ ID NO: 1  (1847)   GAGACTGTTTCTTTTGTTTATACTGACCCTTTAGTTCGGTGACTCTTCTG
   Consensus  (2151)   G ACTGTTTCTTTTGT  AT CT ACCCT T GTT GGTG    CTTCTG
                       2201
SEQ ID NO: 4  (1993)   CAG
SEQ ID NO: 1  (1897)   CAG
   Consensus  (2201)   CAG
```

Fig. 2C

UBIQUITIN REGULATORY ELEMENTS

CROSS REFERENCE

This utility application is a continuation of U.S. patent application Ser. No. 13/429,576 filed Mar. 28, 2012 which is a divisional of U.S. patent application Ser. No. 12/539,137 filed Aug. 11, 2009, now U.S. Pat. No. 8,168,859, and claims the benefit U.S. Provisional Application No. 61/092,205 filed Aug. 27, 2008, all of which are incorporated herein by reference.

FIELD

The present invention relates to the field of plant molecular biology, more particularly to regulation of gene expression in plants.

BACKGROUND

As the field of plant bioengineering develops and more genes become accessible, a greater need exists for transforming with multiple genes. These multiple exogenous genes typically need to be controlled by separate regulatory sequences. Some genes should be regulated constitutively whereas other genes should be expressed at certain developmental stages or location in the transgenic organism. Accordingly, a variety of regulatory sequences having diverse effects is needed.

In addition, undesirable biochemical interactions can result from using the same regulatory sequence to control more than one gene. For example, transformation with multiple copies of a regulatory element may cause homologous recombination between two or more expression systems, formation of hairpin loops caused from two copies of the same promoter or enhancer in opposite orientation in close proximity, competition between identical expression systems for binding to common promoter-specific regulatory factors and inappropriate expression levels of an exogenous gene due to trans effects of a second promoter or enhancer.

In view of these considerations, a goal in this field has been the detection and characterization of new regulatory sequences for transgenic control of DNA constructs.

Isolation and characterization of constitutive promoters and terminators that can serve as regulatory elements for expression of isolated nucleotide sequences of interest in a constitutive manner are needed for improving traits in plants.

SUMMARY

The invention is directed to a promoter from a *Sorghum bicolor* ubiquitin-encoding gene, useful as a regulatory region and providing for constitutive expression of an operably linked nucleotide sequence. The invention is further directed to functional fragments which function to drive constitutive expression of operably linked nucleotide sequences.

Expression cassettes having the nucleotide sequence, plants expressing same and methods of use in driving expression of operably linked nucleotides sequences are within the scope of the invention.

BRIEF DESCRIPTION OF THE FIGURES

FIG. 1: (presented as FIG. 1) The nucleotide sequence of the *sorghum* ubiquitin regulatory element (SEQ ID NO: 1). The promoter (SEQ ID NO: 2) is the first 831 nucleotides, with the intron underlined (SEQ ID NO: 3).

FIG. 2: (presented as FIG. 2A, FIG. 2B and FIG. 2C) A comparison of the *sorghum* ubiquitin regulatory element (promoter and intron) of the invention (SEQ ID NO: 1) with maize ubiquitin promoter region (promoter and intron) (SEQ ID NO: 4).

DETAILED DESCRIPTION

All references referred to are incorporated herein by reference. Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant and/or throughout development, constitutive promoters are utilized. In contrast, where gene expression in response to a stimulus is desired, inducible promoters are the regulatory element of choice. Where expression in specific tissues or organs are desired, tissue-specific promoters may be used. That is, they may drive expression in specific tissues or organs. Such tissue-specific promoters may be temporally constitutive or inducible. In either case, additional regulatory sequences upstream and/or downstream from a core promoter sequence may be included in expression constructs of transformation vectors to bring about varying levels of expression of heterologous nucleotide sequences in a transgenic plant.

In accordance with the invention, nucleotide sequences are provided that allow regulation of transcription in a constitutive manner. Thus, the compositions of the present invention comprise novel nucleotide sequences for plant regulatory elements natively associated with the nucleotide sequences coding for *Sorghum bicolor* ubiquitin protein, herein identified as SB-UBI.

Ubiquitin is a polypeptide found in all eukaryotes and has been studied for its role in a wide range of cellular functions. Promoters of the ubiquitin gene have been isolated. For example, in U.S. Pat. Nos. 5,510,474, 5,614,399, 6,054,574 and 6,020,190 to Quail is described ubiquitin promoters which include a heat shock element and intron. Jilka, et al., describe another maize ubiquitin type promoter at U.S. Pat. No. 6,977,325. Xia, et al., identified a soybean genomic clone containing a ubiquitin gene (Xia, et al., (1994) *Plant Physiol.* 104:805-806). These sequences are reported at GenBank accession numbers D16248.1 and D2823.1. Also, Finer, et al., have discussed analysis of a soybean ubiquitin promoter, but did not provide a sequence (Finer, et al., (2006) "Characterization of soybean promoters through evaluation of GFP expression in transgenic soybean" The 11th Biennial Conference on the Molecular and Cellular Biology of the Soybean, August 5-8, 2006, University of Nebraska, Lincoln, Nebr.).

In an embodiment, the regulatory element drives transcription in a constitutive manner, wherein said regulatory element comprises a nucleotide sequence selected from the group consisting of: a) sequences natively associated with, and that regulate expression of DNA coding for *sorghum* SB-UBI (*Sorghum bicolor* ubiquitin protein); b) the nucleotide sequence set forth in SEQ ID NO: 1, 2 or 3 or c) a sequence comprising a fragment of the nucleotide sequence set forth in either of SEQ ID NO: 1, 2 or 3.

Further embodiments are to expression cassettes, transformation vectors, plants, plant cells and plant cells comprising the above nucleotide sequences. The invention is further to methods of using the sequence in plants and plant cells.

A method for expressing an isolated nucleotide sequence in a plant using the regulatory sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a constitutive manner.

Alternatively, it might be desirable to inhibit expression of a native DNA sequence within a plant's tissues to achieve a desired phenotype. In this case, such inhibition might be accomplished with transformation of the plant to comprise a tissue-specific promoter operably linked to an antisense nucleotide sequence, such that tissue-specific expression of the antisense sequence produces an RNA transcript that interferes with translation of the mRNA of the native DNA sequence in a subset of the plant's cells.

Under the regulation of the regulatory element will be a particular polynucleotide sequence of interest. Expression of the sequence of interest will provide for modification of the phenotype of the plant. Such modification includes modulating the production of an endogenous product, as to amount, relative distribution or the like or production of an exogenous expression product to provide for a novel function or product in the plant.

By "constitutive" is intended expression which is capable of transcribing operatively linked DNA sequences efficiently and expressing said DNA sequences in multiple tissues.

By "regulatory element" is intended sequences responsible expression of the associated coding sequence including, but not limited to, promoters, terminators, enhancers, introns and the like.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomal binding sites, transcriptional start and stop sequences, translational start and stop sequences, activator sequence and the like.

In the same manner, the promoter elements which enable constitutive expression can be identified, isolated and used with other core promoters to confirm constitutive expression. By core promoter is meant the minimal sequence required to initiate transcription, such as the sequence called the TATA box which is common to promoters in genes encoding proteins. Thus the upstream promoter of SB-UBI can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive constitutive expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element and the like.

The promoter of the present invention can be isolated from the 5' region of its native coding region or 5' untranslated region (5' UTR). Likewise the terminator can be isolated from the 3' region flanking its respective stop codon.

The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art. One method is the use of primers and genomic DNA used in conjunction with the Genome Walker Kit™ (Clonetech).

The SB-UBI promoter region set forth in SEQ ID NO: 1 is 1899 nucleotides in length and includes the promoter of SEQ ID NO: 2 which is 831 nucleotides in length and an intron of SEQ ID NO: 3 which is 1068 nucleotides in length. The SB-UBI promoter was isolated from the *sorghum bicolor* SB-UBI coding region. It was isolated by identifying the *sorghum* homolog of the maize ubiquitin, then examining a collection of *sorghum* genomic sequence and looking for hits. Once a hit was identified, the sequence upstream of the open reading frame was used to design PCR primers to amplify a product similar in length to the maize ubiquitin promoter.

The regulatory regions of the invention may be isolated from any plant, including, but not limited to *sorghum* (*Sorghum bicolor, Sorghum vulgare*), corn (*Zea mays*), canola (*Brassica napus, Brassica rapa* ssp.), alfalfa (*Medicago sativa*), rice (*Oryza sativa*), rye (*Secale cereale*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals and conifers. Preferably, plants include corn, soybean, sunflower, safflower, canola, wheat, barley, rye, alfalfa and *sorghum*.

Maize promoters have been used repeatedly to drive expression of genes in non-maize plants, including tobacco (Yang and Russell, (1990); Geffers, et al., (2000); Vilardell, et al., (1991)), cultured rice cells (Vilardell, et al., (1991)), wheat (Oldach, et al., (2001); Brinch-Pedersen, et al., (2003)), rice (Cornejo, et al., (1993); Takimoto, et al., (1994)), sunflower (Roussell, et al., (1988)) and protoplasts of carrot (Roussell, et al., (1988)).

Regulatory sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993) and *Current Protocols in Molecular Biology*, Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg, et al., (2004) *Gene* 341:49-58. Such fragments should retain promoter activity, particularly the ability to drive expression in constitutively. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See, particularly, Mullis, et al., (1987) *Methods Enzymol.* 155:335-350 and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see, e.g., Innis, et al., (1990) *PCR Protocols, A Guide to Methods and Applications*, eds., Academic Press).

The constitutive regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a regulatory region and a second sequence, wherein the regulatory sequence initiates and mediates transcription of the DNA sequence corresponding to the second sequence. The expression cassette will include 5' and 3' regulatory sequences operably linked to at least one of the sequences of the invention.

In one typical embodiment, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994.

The regulatory elements of the invention can be operably linked in expression cassettes along with isolated nucleotide sequences of interest for constitutive expression in the desired plant. Such an expression cassette is provided with a plurality of restriction sites for insertion of the nucleotide sequence of interest under the transcriptional control of the regulatory elements. Alternatively, a specific result can be achieved by providing for a reduction of expression of one or more endogenous products, particularly enzymes or cofactors in the plant. This down regulation can be achieved through many different approaches known to one skilled in the art, including antisense, cosuppression, use of hairpin formations or others and discussed infra. Importation or exportation of a cofactor also allows for control of plant composition. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance and grain characteristics. Still other categories of transgenes include genes for inducing expression of exogenous products such as enzymes, cofactors and hormones from plants and other eukaryotes as well as prokaryotic organisms.

Modifications that affect grain traits include increasing the content of oleic acid or altering levels of saturated and unsaturated fatty acids. Likewise, the level of plant proteins, particularly modified proteins that improve the nutrient value of the plant, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 1994/16078 filed Apr. 10, 1997; WO 1996/38562 filed Mar. 26, 1997; WO 1996/38563 filed Mar. 26, 1997 and U.S. Pat. No. 5,703,409 issued Dec. 30, 1997. Another example is lysine and/or sulfur-rich plant protein encoded by the soybean 2S albumin described in WO 1997/35023 filed Mar. 20, 1996 and the chymotrypsin inhibitor from barley, Williamson, et al., (1987) *Eur. J. Biochem.* 165:99-106.

Agronomic traits in plants can be improved by altering expression of genes that: affect the response of plant growth and development during environmental stress, Cheikh-N, et al., (1994) *Plant Physiol.* 106(1):45-51 and genes controlling carbohydrate metabolism to reduce kernel abortion in maize, Zinselmeier, et al., (1995) *Plant Physiol.* 107(2):385-391.

It is recognized that any gene of interest, including the native coding sequence, can be operably linked to the regulatory elements of the invention and expressed in the plant.

Commercial traits in plants can be created through the expression of genes that alter starch or protein for the production of paper, textiles, ethanol, polymers or other materials with industrial uses.

Means of increasing or inhibiting a protein are well known to one skilled in the art and, by way of example, may include, transgenic expression, antisense suppression, co-suppression methods, including but not limited to: RNA interference, gene activation or suppression using transcription factors and/or repressors, mutagenesis including transposon tagging, directed and site-specific mutagenesis, chromosome engineering (see, Nobrega, et. al., (2004) *Nature* 431:988-993), homologous recombination, TILLING (Targeting Induced Local Lesions In Genomes) and biosynthetic competition to manipulate, the expression of proteins. Many techniques for gene silencing are well known to one of skill in the art, including but not limited to knock-outs (such as by insertion of a transposable element such as Mu, Vicki Chandler, *The Maize Handbook* chapter 118 (Springer-Verlag 1994) or other genetic elements such as a FRT, Lox or other site specific integration site; RNA interference (Napoli, et al., (1990) *Plant Cell* 2:279-289; U.S. Pat. No. 5,034,323, Sharp (1999) *Genes Dev.* 13:139-141, Zamore, et al., (2000) *Cell* 101:25-33 and Montgomery, et al., (1998) *PNAS USA* 95:15502-15507); virus-induced gene silencing (Burton, et al., (2000) *Plant Cell* 12:691-705 and Baulcombe (1999) *Curr. Op. Plant Bio.* 2:109-113); target-RNA-specific ribozymes (Haseloff, et al., (1988) *Nature* 334:585-591); hairpin structures (Smith, et al., (2000) *Nature* 407:319-320; WO 1999/53050 and WO 1998/53083); MicroRNA (Aukerman and Sakai, (2003) *Plant Cell* 15:2730-2741); ribozymes (Steinecke, et al., (1992) *EMBO J.* 11:1525 and Perriman, et al., (1993) *Antisense Res. Dev.* 3:253); oligonucleotide mediated targeted modification (e.g., WO 2003/076574 and WO 1999/25853); zinc-finger targeted molecules (e.g., WO 2001/52620; WO 2003/048345 and WO 2000/42219) and other methods or combinations of the above methods known to those of skill in the art.

Any method of increasing or inhibiting a protein can be used in the present invention. Several examples are outlined in more detail below for illustrative purposes.

The nucleotide sequence operably linked to the regulatory elements disclosed herein can be an antisense sequence for a targeted gene. (See, e.g., Sheehy, et al., (1988) *PNAS USA* 85:8805-8809; and U.S. Pat. Nos. 5,107,065; 5,453,566 and 5,759,829). By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant.

As noted, other potential approaches to impact expression of proteins in the plant include traditional co-suppression, that is, inhibition of expression of an endogenous gene through the expression of an identical structural gene or gene fragment introduced through transformation (Goring, et al., (1991) *Proc. Natl. Acad Sci. USA* 88:1770-1774 co-suppression; Taylor, (1997) *Plant Cell* 9:1245; Jorgensen, (1990) *Trends Biotech.* 8(12):340-344; Flavell, (1994) *PNAS USA* 91:3490-3496; Finnegan, et al., (1994) *Bio/Technology* 12:883-888 and Neuhuber, et al., (1994) *Mol. Gen. Genet.* 244:230-241). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said plant cell. (See, U.S. Pat. No. 5,283,184). The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing (see, Smith, et al., (2000) *Nature* 407:319-320, Waterhouse and Helliwell, (2003)) *Nat. Rev. Genet.* 4:29-38; Waterhouse, et al., (1998) *Proc. Natl. Acad. Sci. USA* 95:13959-13964; Chuang and Meyerowitz, (2000) *Proc. Natl. Acad. Sci. USA* 97:4985-4990; Stoutjesdijk, et al., (2002) *Plant Phystiol.* 129:1723-1731 and PCT Patent Application Numbers WO 1999/53050; WO 1999/49029; WO 1999/61631; WO 2000/49035 and U.S. Pat. No. 6,506,559.

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a gene of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242 and methods for using zinc finger proteins to inhibit the expression of genes in plants are described, for example, in US Patent Publication Number 2003/0037355.

The regulatory region of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the SB-UBI promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (EP Patent Application Number 0 342 926); the promoter for the small subunit of ribulose-1,5-bis-phosphate carboxylase (ss-RUBISCO) (Coruzzi, et al., (1984); Broglie, et al., (1984)) or promoters from the tumor-inducing plasmids from *Agrobacterium tumefaciens*, such as the nopaline synthase, octopine synthase and mannopine synthase promoters (Velten and Schell, (1985)) that have plant activity; or viral promoters such as the cauliflower mosaic virus (CaMV) 19S and 35S promoters (Guilley, et al., (1982); Odell, et al., (1985)), the figwort mosaic virus FLt promoter (Maiti, et al., (1997)) or the coat protein promoter of TMV (Grdzelishvili, et al., (2000)).

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the instant invention. See, Ward, et al., (1993). Exemplary inducible promoters include ecdysone receptor promoters, U.S. Pat. No. 6,504,082; promoters from the ACE1 system which responds to copper (Mett, et al., (1993)); In2-1 and In2-2 gene from maize which respond to benzenesulfonamide herbicide safeners (U.S. Pat. No. 5,364,780; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena, et al., (1991) and McNellis, et al., (1998) and tetracycline-inducible and tetracycline-repressible promoters (see, for example, Gatz, et al., (1991) and U.S. Pat. Nos. 5,814,618 and 5,789,156). Alternatively, plant promoters such as heat shock promoters for example soybean hsp 17.5-E (Gurley, et al., (1986)) or ethanol-inducible promoters (Caddick, et al., (1998)) may be used. See, International Patent Application Number WO 1991/19806 for a review of illustrative plant promoters suitably employed in the present invention.

Constitutive promoters can be utilized to target enhanced transcription and/or expression within a particular plant tissue. Promoters may express in the tissue of interest, along with expression in other plant tissue, may express strongly in the tissue of interest and to a much lesser degree than other tissue or may express highly preferably in the tissue of interest. Constitutive promoters include those described in Yamamoto, et al., (1997); Kawamata, et al., (1997); Hansen, et al., (1997); Russell, et al., (1997); Rinehart, et al., (1996); Van Camp, et al., (1996); Canevascini, et al., (1996); Yamamoto, et al., (1994); Lam, (1994); Orozco, et al., (1993); Matsuoka, et al., (1993) and Guevara-Garcia, et al., (1993).

The expression cassette may also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source. Thus, any convenient termination regions can be used in conjunction with the promoter of the invention, and are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., 1989) *Nucleic Acids Res.* 17:7891-7903; Joshi, et al., (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein, et al., (1989) *Proc. Natl. Acad. Sci. USA* 86:6126-6130; potyvirus leaders, for example, TEV leader (Tobacco Etch Virus), Allison, et al., (1986); MDMV leader (Maize Dwarf Mosaic Virus), *Virology* 154:9-20; human immunoglobulin heavy-chain binding protein (BiP), Macejak, et al., (1991) *Nature* 353:90-94; untranslated leader from the coat protein mRNA of alfalfa mosaic virus (AMV RNA 4), Jobling, et al., (1987) *Nature* 325:622-625); tobacco mosaic virus leader (TMV), Gallie, et al., (1989) *Molecular Biology of RNA*, pages 237-256 and maize chlorotic mottle virus leader (MCMV), Lommel, et al., (1991) *Virology* 81:382-385. See also, Della-Cioppa, et al., (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast or to the endoplasmic reticulum or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites or the like. For this purpose, in vitro mutagenesis, primer repair, restriction digests, annealing and resubstitutions such as transitions and transversions, can be involved.

Reporter genes can be included in the transformation vectors. Examples of suitable reporter genes known in the art can be found in, for example, Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *BioTechniques* 19:650-655 and Chiu, et al., (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella, et al., (1983) *EMBO J.* 2:987-992; methotrexate, Herrera Estrella, et al., (1983) *Nature* 303:209-213; Meijer, et al., (1991) *Plant Mol. Biol.* 16:807-820; hygromycin, Waldron, et al., (1985) *Plant Mol. Biol.* 5:103-108; Zhijian, et al., (1995) *Plant Science* 108:219-227; streptomycin, Jones, et al., (1987) *Mol. Gen. Genet.* 210:86-91; spectinomycin, Bretagne-Sagnard, et al., (1996) *Transgenic Res.* 5:131-137; bleomycin, Hille, et al., (1990) *Plant Mol. Biol.* 7:171-176; sulfonamide, Guerineau, et al., (1990) *Plant Mol. Biol.* 15:127-136; bromoxynil, Stalker, et al., (1988) *Science* 242:419-423; glyphosate, Shaw, et al., (1986) *Science* 233:478-481; phosphinothricin, DeBlock, et al., (1987) *EMBO J.* 6:2513-2518.

Further, when linking a promoter of the invention with a nucleotide sequence encoding a detectable protein, expression of a linked sequence can be tracked in the plant, thereby providing a useful so-called screenable or scorable markers. The expression of the linked protein can be detected without the necessity of destroying tissue. More recently, interest has increased in utilization of screenable or scorable markers. By way of example without limitation, the promoter can be linked with detectable markers including a β-glucuronidase, or uidA gene (GUS), which encodes an enzyme for which various chromogenic substrates are known (Jefferson, et al., (1986) *Proc. Natl. Acad. Sci. USA* 83:8447-8451); chloramphenicol acetyl transferase; alkaline phosphatase; a R-locus gene, which encodes a product that regulates the production of anthocyanin pigments (red color) in plant tissues (Dellaporta, et al., in *Chromosome Structure and Function*, Kluwer Academic Publishers, Appels and Gustafson eds., pp. 263-282 (1988); Ludwig, et al., (1990) *Science* 247:449); a p-lactamase gene (Sutcliffe, (1978) *Proc. Nat'l. Acad. Sci. U.S.A.* 75:3737), which encodes an enzyme for which various chromogenic substrates are known (e.g., PADAC, a chromogenic cephalosporin); a xyIE gene (Zukowsky, et al., (1983) *Proc. Nat'l. Acad. Sci. U.S.A.* 80:1101), which encodes a catechol dioxygenase that can convert chromogenic catechols; an α-amylase gene (Ikuta, et al., (1990) *Biotech.* 8:241); a tyrosinase gene (Katz, et al., (1983) *J. Gen. Microbiol.* 129:2703), which encodes an enzyme capable of oxidizing tyrosine to DOPA and dopaquinone, which in turn condenses to form the easily detectable compound melanin a green fluorescent protein (GFP) gene (Sheen, et al., (1995) *Plant J.* 8(5):777-84); a lux gene, which encodes a luciferase, the presence of which may be detected using, for example, X-ray film, scintillation counting, fluorescent spectrophotometry, low-light video cameras, photon counting cameras or multiwell luminometry (Teeri, et al., (1989) *EMBO J.* 8:343); DS-RED EXPRESS (Matz, et al., (1999) *Nature Biotech.* 17:969-973, Bevis, et al., (2002) *Nature Biotech* 20:83-87, Haas, et al., (1996) *Curr. Biol.* 6:315-324); *Zoanthus* sp. yellow fluorescent protein (ZsYellow) that has been engineered for brighter fluorescence (Matz, et al., (1999) *Nature Biotech.* 17:969-973, available from BD Biosciences Clontech, Palo Alto, Calif., USA, catalog number K6100-1); and cyan florescent protein (CYP) (Bolte, et al., (2004) *J. Cell Science* 117:943-54 and Kato, et al., (2002) *Plant Physiol* 129:913-42).

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in E. coli are discussed in Sambrook, et al., (supra). The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector. Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included.

A transformation vector comprising the particular regulatory sequences of the present invention, operably linked to an isolated nucleotide sequence of interest in an expression cassette, can be used to transform any plant. In this manner, genetically modified plants, plant cells, plant tissue and the like can be obtained. Transformation protocols can vary depending on the type of plant or plant cell, i.e., monocot or dicot, targeted for transformation. Suitable methods of transforming plant cells include microinjection, Crossway, et al., (1986) *Biotechniques* 4:320-334; electroporation, Riggs, et al., (1986) *Proc. Natl. Acad. Sci. USA* 83:5602-5606; *Agrobacterium*-mediated transformation, see, for example, Townsend, et al., U.S. Pat. No. 5,563,055; direct gene transfer, Paszkowski, et al., (1984) *EMBO J.* 3:2717-2722 and ballistic particle acceleration, see for example, Sanford, et al., U.S. Pat. No. 4,945,050, Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926. Also see, Weissinger, et al., (1988) *Annual Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Datta, et al., (1990) *Bio/Technology* 8:736-740 (rice); Klein, et al., (1988) *Proc. Natl. Acad. Sci. USA* 85:4305-4309 (maize); Klein, et al., (1988) *Biotechnology* 6:559-563 (maize); Klein, et al., (1988) *Plant Physiol.* 91:440-444 (maize); Fromm, et al., (1990) *Biotechnology* 8:833-839; Hooydaas-Van Slogteren, et al., (1984) *Nature (London)* 311:763-764; Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*).

The cells that have been transformed can be grown into plants in accordance with conventional methods. See, for example, McCormick, et al., (1986) *Plant Cell Reports* 5:81-84. These plants can then be grown and pollinated with the same transformed strain or different strains. The resulting plant having constitutive expression of the desired phenotypic characteristic can then be identified. Two or more generations can be grown to ensure that constitutive expression of the desired phenotypic characteristic is stably maintained and inherited.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants and selection for plants from subsequent generations which express the amino acid sequence. The plant breeding methods used herein are well known to one skilled in the art. For a discussion of plant breeding techniques, see, Poehlman and Sleper, (1995) *Breeding field crops*, 4$^{th}$ Edition, Iowa State University Press. Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile and the other the male fertile pollen donor. This can be accomplished by hand detasslling, cytoplasmic male sterility or control of male sterility through a variety of methods well known to the skilled breeder. Examples of more sophisticated male sterility systems include those described by Brar, et al., U.S. Pat. Nos. 4,654,465 and 4,727,219 and Albertsen, et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Poehlman, et al., (1995). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

The following examples are offered by way of illustration and not by way of limitation.

EXAMPLES

Example 1

Isolation of Regulatory Sequences

Regulatory regions from maize SB-UBI (*Sorghum bicolor* ubiquitin protein) were isolated from *sorghum* plants and cloned. *Sorghum* SB-UBI was selected as a source of constitutive regulatory elements based on the spatial and temporal expression of its products.

The promoter region consists of a promoter region and an intron which together are an 1899 base pair nucleotide sequence, shown in FIG. 1. The promoter is 831 nucleotides, with the intron 1068 nucleotides and which is underlined. A BLAST of GenBank showed the highest identity was 60% to GenBank accession number DQ225752, GI81238239, Upadhyaya, et al., "Immobile Ac/T-DNA vector pNU400, complete sequence" July 2006. (Dissociation (Ds) constructs, mapped Ds launch pads and a transiently-expressed transposase system suitable for localized insertional mutagenesis in rice, *Theor. Appl. Genet.* 112(7):1326-1341 (2006)). The intron had 98% identity to GenBank accession number AY342494, GI 37912415, Streatfield, et al., "*Zea diploperennis* polyubiquitin-1 (ubi-1) gene, promoter region and 5' UTR" August 2004.

Using the maize ubiquitin EST, the *sorghum* ortholog was identified from an EST collection and used to BLAST a collection of *sorghum* genomic sequences. Once the corresponding *sorghum* genomic region was identified, the upstream and downstream sequences were cloned that were similar in length to the maize ubiquitin promoter, including the intron and the terminator by basing PCR primers on the identified *sorghum* genomic sequence.

Example 2

Expression Data Using Promoter Sequences

A construct, named PHP28501, was prepared which included the *sorghum* ubiquitin promoter with intron of the invention linked with the DS-RED EXPRESS screenable marker, supra and the pinII or proteinase inhibitor II transcription terminator (An, et al., (1989) *Plant Cell* 1:115-122). All vectors are constructed using standard molecular biology techniques (Sambrook, et al., supra). Successful subcloning is confirmed by restriction analysis. Transformation and expression can be confirmed by the methods outlined in Example 3.

Example 3

Transformation and Regeneration of Maize Callus Via *Agrobacterium*

Constructs used were as those set forth supra using a binary plasmid with the left and right borders (see, Hiei, et al., U.S. Pat. No. 7,060,876) and the selectable marker for maize-optimized PAT (phosphinothricin acetyl transferase). Jayne, et al., U.S. Pat. No. 6,096,947.

Preparation of *Agrobacterium* Suspension:

*Agrobacterium* was streaked out from a −80° C. frozen aliquot onto a plate containing PHI-L medium and was cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) was added to a concentration of 50 mg/l in sterile ddH$_2$O (stock solution A: K$_2$HPO$_4$ 60.0 g/l, NaH$_2$PO$_4$ 20.0 g/l, adjust pH to 7.0 w/KOH and autoclaved; stock solution B: NH$_4$Cl 20.0 g/l, MgSO$_4$.7H$_2$O 6.0 g/l, KCl 3.0 g/l, CaCl$_2$ 0.20 g/l, FeSO$_4$.7H$_2$O 50.0 mg/l, autoclaved; stock solution C: glucose 5.56 g/l, agar 16.67 g/l (#A-7049, Sigma Chemicals, St. Louis, Mo.) and was autoclaved).

The plate can be stored at 4° C. and used usually for about 1 month. A single colony was picked from the master plate and was streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and was incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2, 4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) was added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension is adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobacterium* suspension was aliquoted into 2 ml microcentrifuge tubes, each containing 1 ml of the suspension. The suspensions were then used as soon as possible.

Embryo Isolation, Infection and Co-Cultivation:

About 2 ml of the same medium (here PHI-A or PHI-I) which is used for the *Agrobacterium* suspension was added into a 2 ml microcentrifuge tube. Immature embryos were isolated from a sterilized ear with a sterile spatula (Baxter Scientific Products S1565) and dropped directly into the medium in the tube. A total of about 100 embryos are placed in the tube. The optimal size of the embryos was about 1.0-1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension was added to the embryos and the tube is vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; silver nitrate 0.85 mg/l; Gelrite® (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm® tape or Pylon Vegetative Combine Tape (product named "E.G.CUT" and is available in 18 mm×50 m sections; Kyowa Ltd., Japan) and was incubated in the dark at 23-25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm® or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months.

The herbicide-resistant calli are then "bulked up" by growing on the same medium for another two weeks until the diameter of the calli is about 1.5-2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; Gelrite® 1.5 g/l; pH 5.6] at 25° C. under a daylight schedule of 16 hr light (270 uE m-2sec-1) and 8 hr dark until shoots and roots are developed. Each small plantlet was then transferred to a 25×150 mm tube containing PHI-F medium and is grown under the same conditions for approximately another week. The plants were transplanted to pots with soil mixture in a greenhouse. DS-RED EXPRESS events are determined at the callus stage or regenerated plant stage.

Ability of the SB-UBI promoter and truncated variant to drive expression in maize was confirmed by DS-RED EXPRESS detection in plant tissue by the procedures outlined supra.

Although the foregoing invention has been described in some detail by way of illustration and example for purposes of clarity of understanding, it will be obvious that certain changes and modifications may be practiced within the scope of the appended claims. All references cited are incorporate herein by reference.

What is claimed is:

1. A regulatory element that drives transcription in a constitutive manner, wherein the regulatory element comprises a nucleotide sequence selected from the group consisting of:
    a) the nucleotide sequence of SEQ ID NO: 1, 2 or 3; and
    b) a nucleotide sequence that is at least 90% identical to the nucleotide sequence of SEQ ID NOS: 1 or 2 wherein, the regulatory element is operably linked to a heterologous nucleotide sequence.

2. An expression cassette comprising a regulatory element operably linked to a nucleotide sequence wherein the regulatory element comprises the nucleotide sequence of claim 1.

3. A plant stably transformed with an expression cassette of claim 2.

4. The plant of claim 3, wherein said plant is a monocot.

5. The plant of claim 3, wherein said monocot is maize, wheat, rice, barley, *sorghum* or rye.

6. Seed of the plant of claim 3 wherein the seed comprises the expression cassette.

7. A method for selectively expressing a nucleotide sequence in a plant cell, the method comprising:

a) transforming a plant cell with an expression cassette, the expression cassette comprising a regulatory element, wherein the regulatory element comprises a nucleotide sequence selected from the group consisting of:
      i) the nucleotide sequence set forth in SEQ ID NO: 1, 2 or 3; and
      ii) a nucleotide sequence that is at least 90% identical to the nucleotide sequence of SEQ ID NOS: 1 or 2; wherein the regulatory element drives the expression of a heterologous nucleotide sequence and
   b) growing the plant cell to selectively express the nucleotide sequence.

8. The method of claim 7 further comprising regenerating a stably transformed plant from the plant cell; wherein expression of the nucleotide sequence alters the phenotype of a plant.

9. The plant of claim 8, wherein said plant is a monocot.

10. The plant of claim 8, wherein said monocot is maize, wheat, rice, barley, *sorghum* or rye.

11. Seed of the plant of claim 8 wherein the seed comprises the expression cassette.

* * * * *

SEQUENCE LISTING

```
<160> NUMBER OF SEQ ID NOS: 6

<210> SEQ ID NO 1
<211> LENGTH: 1899
<212> TYPE: DNA
<213> ORGANISM: Sorghum bicolor
<220> FEATURE:
<221> NAME/KEY: promoter
<222> LOCATION: (1)...(831)
<221> NAME/KEY: intron
<222> LOCATION: (832)...(1899)

<400> SEQUENCE: 1
ctgcccttaa ggccaattgt tcaagattca ttcaacaatt gaaacatctc ccatgattaa      60
atcagtataa ggttgctatg gtcttgcttg acaaagtttt tttttgaggg aatttcaact     120
aaatttttga gtgaaactat caaatactga ttttaaaaaa tttttataaa aggaagcgca     180
gagataaaag gccatctatg ctacaaaagt acccaaaaat gtaatcctaa agtatgaatt     240 gcatttttt tttgtttgga cgaaaggaaa ggagtattac cacaagaatg atatcatctt     300
catatttaga tcttttttgg gtaaagcttg agattctcta aatatagaga aatcagaaga     360
aaaaaaaacc gtgttttggt ggttttgatt tctagcctcc acaataactt tgacggcgtc     420
gacaagtcta acggacacca agcagcgaac caccagcgcc gagccaagcg aagcagacgg     480
ccgagacgtt gacaccttcg gcgcggcatc tctcgagagt tccgctccgg cgctccacct     540
ccaccgctgg cggtttctta ttccgttccg ttccgcctcc tgctctgctc ctctccacac     600
cacacggcac gaaaccgtta cggcaccggc agcacccagc acgggagagg ggattcctttt     660
```

```
cccaccgttc cttcccttc cgccccgccg ctataaatag ccagccccat ccccagcttt    720
tttccccaat ctcatctcct ctctcctgtt gttcggagca cacgcacaat ccgatcgatc    780
cccaaatccc cttcgtctct cctcgcgagc tcgtggatc ccagcttcaa ggtacggcga    840
tcgatcatcc ccctccttc tctctacctt cttttctcta gactacatcg gatggcgatc    900
catggttagg gcctgctagt ttcccttcct gttttgtcga tggctgcgag gcacaataga    960
tctgatggcg ttatgacggc taacttgtca tgttgttgcg atttatagtc cctttaggag   1020
atcagtttaa tttctcggat ggttcgagat cggtggtcca tggttagtac cctaagatcc   1080
gcgctgttag ggttcgtaga tggaggcgac ctgttctgat tgttaacttg tcagtacctg   1140
ggaaatcctg ggatggttct agctcgtccg cagatgagat cgatttcatg atcctctgta   1200
tcttgtttcg ttgcctaggt tccgtctaat ctatccgtgg tatgatgtag atgttttgat   1260
cgtgctaact acgtcttgta aagttaattg tcaggtcata atttttagca tgcctttttt   1320
tttgtttggt tttgtctaat tgggctgtcg ttctagatca gagtagaaga ctgttccaaa   1380
ctacctgctg gatttattga acttggatct gtatgtgtgt cacatatctt cataaattca   1440
tgattaagat ggattgaaat atcttttatc ttttttggtat ggatagttct atatgttggt   1500
gtggcttgt tagatgtata catgcttaga tacatgaagc aacgtgctgc tactgtttag   1560
taattgctgt tcatttgtct aataaacaga taaggatatg tatttatgtt gctgttggtt   1620
ttgctggtac tttgttggat acaaatgctt caatacagaa aacagcatgc tgctacgatt   1680
taccatttat ctaatcttat catatgtcta atctaataaa caaacatgct tttaaattat   1740
cttcatatgc ttggatgatg gcatacacag cggctatgtg tggtttttta aatacccagc   1800
atcatgggca tgcatgacac tgctttaata tgctttttat ttgcttgaga ctgtttcttt   1860
tgtttatact gacccttag ttcggtgact cttctgcag                          1899

<210> SEQ ID NO 2
<211> LENGTH: 831
<212> TYPE: DNA
<213> ORGANISM: Sorghum bicolor

<400> SEQUENCE: 2
ctgcccttaa ggccaattgt tcaagattca ttcaacaatt gaaacatctc ccatgattaa    60
atcagtataa ggttgctatg gtcttgcttg acaaagtttt ttttgagggg aatttcaact   120
aaatttttga gtgaaactat caaatactga ttttaaaaaa tttttataaa aggaagcgca   180
gagataaaag gccatctatg ctacaaaagt acccaaaat gtaatcctaa agtatgaatt    240
gcatttttt tttgtttgga cgaaaggaaa ggagtattac cacaagaatg atatcatctt   300
catatttaga tctttttggg gtaaagcttg agattctcta aatatagaga atcagaaga    360
aaaaaaaacc gtgttttggt ggttttgatt tctagcctcc acaataactt tgacggcgtc   420
gacaagtcta acggacacca agcagcgaac caccagcgcc gagccaagcg aagcagacgg   480
ccgagacgtt gacaccttcg gcgcggcatc tctcgagagt tccgctccgg cgctccacct   540
ccaccgctgg cggttcttta ttccgttccg ttcgcctcc tgctctgctc ctctccacac   600
cacacggcac gaaaccgtta cggcaccggc agcacccagc acgggagagg ggattccttt   660
cccaccgttc cttcccttc cgccccgccg ctataaatag ccagccccat ccccagcttt   720
tttccccaat ctcatctcct ctctcctgtt gttcggagca cacgcacaat ccgatcgatc   780
cccaaatccc cttcgtctct cctcgcgagc tcgtggatc ccagcttcaa g             831
```

<210> SEQ ID NO 3
<211> LENGTH: 1068
<212> TYPE: DNA
<213> ORGANISM: Sorghum bicolor

<400> SEQUENCE: 3

| | | | | | |
|---|---|---|---|---|---|
| gtacggcgat | cgatcatccc | ccctccttct | ctctaccttc | ttttctctag | actacatcgg | 60 |
| atggcgatcc | atggttaggg | cctgctagtt | tcccttcctg | ttttgtcgat | ggctgcgagg | 120 |
| cacaatagat | ctgatggcgt | tatgacggct | aacttgtcat | gttgttgcga | tttatagtcc | 180 |
| ctttaggaga | tcagtttaat | ttctcggatg | gttcgagatc | ggtggtccat | ggttagtacc | 240 |
| ctaagatccg | cgctgttagg | gttcgtagat | ggaggcgacc | tgttctgatt | gttaacttgt | 300 |
| cagtacctgg | gaaatcctgg | gatggttcta | gctcgtccgc | agatgagatc | gatttcatga | 360 |
| tcctctgtat | cttgtttcgt | tgcctaggtt | ccgtctaatc | tatccgtggt | atgatgtaga | 420 |
| tgttttgatc | gtgctaacta | cgtcttgtaa | agttaattgt | caggtcataa | tttttagcat | 480 |
| gccttttttt | ttgtttggtt | ttgtctaatt | gggctgtcgt | tctagatcag | agtagaagac | 540 |
| tgttccaaac | tacctgctgg | atttattgaa | cttggatctg | tatgtgtgtc | acatatcttc | 600 |
| ataaattcat | gattaagatg | gattgaaata | tcttttatct | ttttggtatg | atagttcta | 660 |
| tatgttggtg | tggctttgtt | agatgtatac | atgcttagat | acatgaagca | acgtgctgct | 720 |
| actgtttagt | aattgctgtt | catttgtcta | ataaacagat | aaggatatgt | atttatgttg | 780 |
| ctgttggttt | tgctggtact | tgttggata | caaatgcttc | aatacagaaa | acagcatgct | 840 |
| gctacgattt | accatttatc | taatcttatc | atatgtctaa | tctaataaac | aaacatgctt | 900 |
| ttaaattatc | ttcatatgct | tggatgatgg | catacacagc | ggctatgtgt | ggttttttaa | 960 |
| atacccagca | tcatgggcat | gcatgacact | gctttaatat | gcttttttatt | tgcttgagac | 1020 |
| tgtttctttt | gtttatactg | acctttagt | tcggtgactc | ttctgcag | | 1068 |

<210> SEQ ID NO 4
<211> LENGTH: 1995
<212> TYPE: DNA
<213> ORGANISM: Zea mays

<400> SEQUENCE: 4

| | | | | | |
|---|---|---|---|---|---|
| tgcagtgcag | cgtgacccgg | tcgtgcccct | ctctagagat | aatgagcatt | gcatgtctaa | 60 |
| gttataaaaa | attaccacat | atttttttg | tcacacttgt | ttgaagtgca | gtttatctat | 120 |
| ctttatacat | atatttaaac | tttactctac | gaataatata | atctatagta | ctacaataat | 180 |
| atcagtgttt | tagagaatca | tataaatgaa | cagttagaca | tggtctaaag | gacaattgag | 240 |
| tattttgaca | acaggactct | acagttttat | cttttttagtg | tgcatgtgtt | ctcctttttt | 300 |
| tttgcaaata | gcttcaccta | tataatactt | catccatttt | attagtacat | ccatttaggg | 360 |
| tttagggtta | atggtttta | tagactaatt | ttttagtac | atctattta | ttctatttta | 420 |
| gcctctaaat | taagaaaact | aaaactctat | tttagttttt | ttatttaata | atttagatat | 480 |
| aaaatagaat | aaaataaagt | gactaaaaat | taaacaaata | cccttttaaga | aattaaaaaa | 540 |
| actaaggaaa | catttttctt | gtttcgagta | gataatgcca | gcctgttaaa | cgccgtcgac | 600 |
| gagtctaacg | gacaccaacc | agcgaaccag | cagcgtcgcg | tcgggccaag | cgaagcagac | 660 |
| ggcacggcat | ctctgtcgct | gcctctggac | ccctctcgag | agttccgctc | caccgttgga | 720 |
| cttgctccgc | tgtcggcatc | cagaaattgc | gtggcggagc | ggcagacgtg | agccggcacg | 780 |
| gcaggcggcc | tcctcctcct | ctcacggcac | cggcagctac | gggggattcc | tttcccaccg | 840 |

```
ctccttcgct ttcccttcct cgcccgccgt aataaataga caccccctcc acaccctctt    900
tccccaacct cgtgttgttc ggagcgcaca cacacacaac cagatctccc ccaaatccac    960
ccgtcggcac ctccgcttca aggtacgccg ctcgtcctcc ccccccccc tctctacctt   1020 ctctagatcg gcgttccggt ccatgcatgg ttagggcccg gtagttctac ttctgttcat   1080
gtttgtgtta gatccgtgtt tgtgttagat ccgtgctgct agcgttcgta cacggatgcg   1140
acctgtacgt cagacacgtt ctgattgcta acttgccagt gtttctcttt ggggaatcct   1200
gggatggctc tagccgttcc gcagacggga tcgatttcat gatttttttt gtttcgttgc   1260 ataggggtttg gtttgccctt ttcctttatt tcaatatatg ccgtgcactt gtttgtcggg   1320 tcatctttc atgctttttt ttgtcttggt tgtgatgatg tggtctggtt gggcggtcgt   1380
tctagatcgg agtagaattc tgtttcaaac tacctggtgg atttattaat tttggatctg   1440
tatgtgtgtg ccatacatat tcatagttac gaattgaaga tgatggatgg aaatatcgat   1500
ctaggatagg tatacatgtt gatgcgggtt ttactgatgc atatacagag atgctttttg   1560
ttcgcttggt tgtgatgatg tggtgtggtt gggcggtcgt tcattcgttc tagatcggag   1620
tagaatactg tttcaaacta cctggtgtat ttattaattt tggaactgta tgtgtgtgtc   1680
atacatcttc atagttacga gtttaagatg gatggaaata tcgatctagg ataggtatac   1740
atgttgatgt gggttttact gatgcatata catgatggca tatgcagcat ctattcatat   1800
gctctaacct tgagtaccta tctattataa taaacaagta tgttttataa ttattttgat   1860
cttgatatac ttggatgatg gcatatgcag cagctatatg tggattttttt tagccctgcc   1920 ttcatacgct atttatttgc ttggtactgt ttcttttgtc gatgctcacc ctgttgtttg   1980
gtgttacttc tgcag                                                   1995

<210> SEQ ID NO 5
<211> LENGTH: 982
<212> TYPE: DNA
<213> ORGANISM: Zea mays

<400> SEQUENCE: 5
tgcagtgcag cgtgacccgg tcgtgcccct ctctagagat aatgagcatt gcatgtctaa     60
gttataaaaa attaccacat attttttttg tcacacttgt ttgaagtgca gtttatctat    120
ctttatacat atatttaaac tttactctac gaataatata atctatagta ctacaataat    180
atcagtgttt tagagaatca tataaatgaa cagttagaca tggtctaaag gacaattgag    240
tattttgaca acaggactct acagttttat ctttttagtg tgcatgtgtt ctccttttt    300 tttgcaaata gcttcaccta tataatactt catccatttt attagtacat ccatttaggg    360 tttaggggtta atggttttta tagactaatt ttttagtac atctatttta ttctatttta    420
gcctctaaat taagaaaact aaaactctat tttagttttt ttatttaata atttagatat    480
aaaatagaat aaaataaagt gactaaaaat taaacaaata ccctttaaga aattaaaaaa    540
actaaggaaa cattttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac ggggattcc tttcccaccg    840 ctccttcgct ttcccttcct cgcccgccgt aataaataga caccccctcc acaccctctt    900
tccccaacct cgtgttgttc ggagcgcaca cacacacaac cagatctccc ccaaatccac    960
```

```
ccgtcggcac ctccgcttca ag                                              982

<210> SEQ ID NO 6
<211> LENGTH: 1013
<212> TYPE: DNA
<213> ORGANISM: Zea mays

<400> SEQUENCE: 6
gtacgccgct cgtcctcccc ccccccctc tctaccttct ctagatcggc gttccggtcc       60
atgcatggtt agggcccggt agttctactt ctgttcatgt ttgtgttaga tccgtgtttg     120
tgttagatcc gtgctgctag cgttcgtaca cggatgcgac ctgtacgtca gacacgttct    180
gattgctaac ttgccagtgt ttctctttgg ggaatcctgg gatggctcta gccgttccgc    240
agacgggatc gatttcatga ttttttttgt ttcgttgcat agggtttggt ttgcccttt     300 cctttatttc aatatatgcc gtgcacttgt ttgtcgggtc atcttttcat gctttttttt    360
gtcttggttg tgatgatgtg gtctggttgg gcggtcgttc tagatcggag tagaattctg    420
tttcaaacta cctggtggat ttattaattt tggatctgta tgtgtgtgcc atacatattc    480
atagttacga attgaagatg atggatggaa atatcgatct aggataggta tacatgttga    540
tgcgggtttt actgatgcat atacagagat gcttttgtt cgcttggttg tgatgatgtg     600
gtgtggttgg gcggtcgttc attcgttcta gatcggagta gaatactgtt tcaaactacc    660
tggtgtattt attaattttg gaactgtatg tgtgtgtcat acatcttcat agttacgagt    720
ttaagatgga tggaaatatc gatctaggat aggtatacat gttgatgtgg gttttactga    780
tgcatataca tgatggcata tgcagcatct attcatatgc tctaaccttg agtacctatc    840
tattataata aacaagtatg ttttataatt attttgatct tgatatactt ggatgatggc    900
atatgcagca gctatatgtg gattttttta gccctgcctt catacgctat ttatttgctt    960
ggtactgttt cttttgtcga tgctcaccct gttgtttggt gttacttctg cag           1013
```